United States Patent
Satoh et al.

(10) Patent No.: US 8,319,155 B2
(45) Date of Patent: Nov. 27, 2012

(54) COLUMN OVEN WITH DOUBLE TEMPERATURE CONTROL

(75) Inventors: Toru Satoh, Yamato (JP); Tadanori Sugimoto, Sagamihara (JP); Minoru Takahashi, Yokohama (JP)

(73) Assignee: Tosoh Corporation, Yamaguchi (JP)

( * ) Notice: Subject to any disclaimer, the term of this patent is extended or adjusted under 35 U.S.C. 154(b) by 655 days.

(21) Appl. No.: 12/528,220

(22) PCT Filed: Feb. 22, 2008

(86) PCT No.: PCT/JP2008/053068
§ 371 (c)(1), (2), (4) Date: Aug. 21, 2009

(87) PCT Pub. No.: WO2008/102872
PCT Pub. Date: Aug. 28, 2008

(65) Prior Publication Data
US 2010/0096380 A1   Apr. 22, 2010

(30) Foreign Application Priority Data
Feb. 23, 2007  (JP) ................ 2007-044379

(51) Int. Cl.
*A21B 1/00* (2006.01)
(52) U.S. Cl. .................. 219/394; 219/400
(58) Field of Classification Search ......... 219/400, 219/394, 395
See application file for complete search history.

(56) References Cited

U.S. PATENT DOCUMENTS

| | | | |
|---|---|---|---|
| 3,846,074 A | 11/1974 | Tulumello et al. | |
| 4,286,456 A | 9/1981 | Sisti et al. | |
| 6,485,543 B1 | 11/2002 | MacDonald et al. | |

FOREIGN PATENT DOCUMENTS

| | | |
|---|---|---|
| FR | 2 298 792 | 8/1976 |
| JP | 48-075697 | 9/1973 |
| JP | 49-085188 | 7/1974 |
| JP | 55-047613 | 3/1980 |
| JP | 62-167473 A | 7/1987 |
| JP | 05-087793 A | 4/1993 |
| JP | 11-201957 A | 7/1999 |
| JP | 2001-013126 A | 1/2001 |
| JP | 2002-055094 A | 2/2002 |
| JP | 2005-140505 A | 6/2005 |
| WO | 2007/138761 A1 | 12/2007 |

OTHER PUBLICATIONS

International Preliminary Report on Patentability and the Written Opinion of the International Searching Authority, corresponding to PCT/JP 2008-053068.

*Primary Examiner* — Richard A. Booth
(74) *Attorney, Agent, or Firm* — Sughrue Mion, PLLC

(57) ABSTRACT

An object in the present invention is to provide a column oven capable of maintaining excellent temperature stability despite ambient temperature changes around the column oven.

A column oven 10 has an outer chamber 12, an inner chamber 14 disposed in the outer chamber 12, and column 16 disposed in the inner chamber 14. The outer chamber includes heater 18, fan 20 for the outer chamber for circulating air heated by the heater 18, and a temperature sensor 22 for the outer chamber for detecting temperature inside the outer chamber. The inner chamber 14 includes fans 24 for the inner chamber and a temperature sensor 26 for the inner chamber for detecting temperature inside the inner chamber. An inner chamber wall is spaced-apart from an outer chamber wall. A target temperature in the outer chamber is set based on temperature detected by the temperature sensor 26 for the inner chamber. A temperature controller 28 controls power distribution to the heater 18 according to temperature detected by the temperature sensor 22 for the outer chamber.

7 Claims, 6 Drawing Sheets

COLUMN OVEN WITH DOUBLE TEMPERATURE CONTROL

RELATED APPLICATIONS

This application claims the priority of Japanese Patent Application No. 2007-044379 filed on Feb. 23, 2007, which is incorporated herein by reference.

FIELD OF THE INVENTION

This invention relates to column oven, and more particularly, to an improved temperature control system thereof.

BACKGROUND OF THE INVENTION

Column ovens have been used in various kinds of chromatographic apparatus such as gas chromatographic apparatus and liquid chromatographic apparatus. A column oven controls the temperature of any columns so that a component to be analyzed or to be preparatively isolated is properly separated. Because the temperature of a column has a great influence on the ability of a packing material to absorb and desorb each major component, high-precision temperature control is required for achieving efficient component separation as well as excellent reproducibilty.

For this reason, a column oven with a double chamber structure (Patent Literatures 1 and 2) or a preheating technique before introducing the outer air into a constant-temperature bath (Patent Literature 3) has been used.

Particularly, a liquid chromatographic apparatus using a mixed solvent and a differential refractometer utilizes a plurality of columns for sample and reference analysis, where the temperature of an effluent from the columns affects the refractive index. Thus, a small temperature change in each column or a temperature difference between the columns affects the stability of a baseline as a noise, and the baseline tends to be destabilized.

Conventional column ovens have not been able to achieve sufficient temperature stability and they have had difficulties in making the maximum use of the abilities of the latest high-sensitivity detectors.

In this regard, as a result of verification with use of a liquid chromatographic apparatus having a differential refractometer, the inventors herein found that key factors affecting destabilization are: on/off operation of a heater, the temperature distribution within an oven, and the ambient temperature change around an oven. Particularly, the temperature distribution in a column chamber is greatly affected by any temperature change and temperature distribution outside the column chamber, even by 0.1° C. increment or decrement.

Patent Literature 1: Japanese Unexamined Patent Application Publication H5-87793.
Patent Literature 2: Japanese Unexamined Patent Application Publication 2005-140505.
Patent Literature 3: Japanese Unexamined Patent Application Publication 2001-13126.

DISCLOSURE OF THE INVENTION

Problem to be Solved by the Invention

The present invention was conceived in light of the above-described problems in the art. The object of the present invention is to provide a column oven capable of maintaining excellent temperature stability despite ambient temperature change around the column oven.

Means to Solve the Problem

In order to achieve the above described object, the present invention provides a column oven comprising:
an outer chamber and an inner chamber disposed in the outer chamber;
one or more columns disposed in the inner chamber;
wherein the outer chamber includes one or more heaters, one or more fans for the outer chamber for circulating air heated by the heaters, and a temperature sensor for the outer chamber for detecting the temperature inside the outer chamber;
wherein the inner chamber includes one or more fans for the inner chamber; and
a controller for controlling power supplied to the heaters according to the temperature detected by the temperature sensor for the outer chamber.

In addition, the present invention provides a column oven comprising:
an outer chamber and an inner chamber disposed in the outer chamber;
one or more columns disposed in the inner chamber;
wherein the outer chamber includes one or more heaters, one or more fans for the outer chamber for circulating air heated by the heaters, and a temperature sensor for the outer chamber for detecting the temperature inside the outer chamber;
wherein the inner chamber includes one or more fans for the inner chamber and a temperature sensor for the inner chamber for detecting the temperature inside the inner chamber; and
a temperature controller for controlling the power supplied to the heaters by comparing the temperature detected by the temperature sensor for the outer chamber with a target temperature in the outer chamber which is set based on the temperature detected by the temperature sensor for the inner chamber.

In addition, it is preferred that the column oven comprise:
one or more sample columns and one or more reference columns, disposed in an inner chamber; and
the column oven is mounted in a liquid chromatographic apparatus having a differential refractometer.

In addition, it is preferred that the column oven is one where:
each of the outer chamber and the inner chamber has a door, and the door of the outer chamber is connected to the door of the inner chamber by one or more connecting members made of elastic material; and
the door of the inner chamber opens in conjunction with opening the door of the outer chamber and it closes in conjunction with closing the door of the outer chamber in a state that the door of the inner chamber is spaced-apart from the door of the outer chamber.

Because the column oven according to the present invention includes an outer chamber, an inner chamber, and one or more heaters disposed in the outer chamber, the outside of the inner chamber where columns are disposed (i.e. the inside of the outer chamber) is kept at a relatively constant temperature, and the column undergoes less affects from any ambient temperature change around the column oven. Thus, the column oven according to the present invention can achieve excellent temperature precision.

BEST MODE FOR CARRYING OUT THE INVENTION

Preferred embodiments of the present invention will be described below based on the drawings.

EXAMPLES

Embodiment 1

Figure 1:
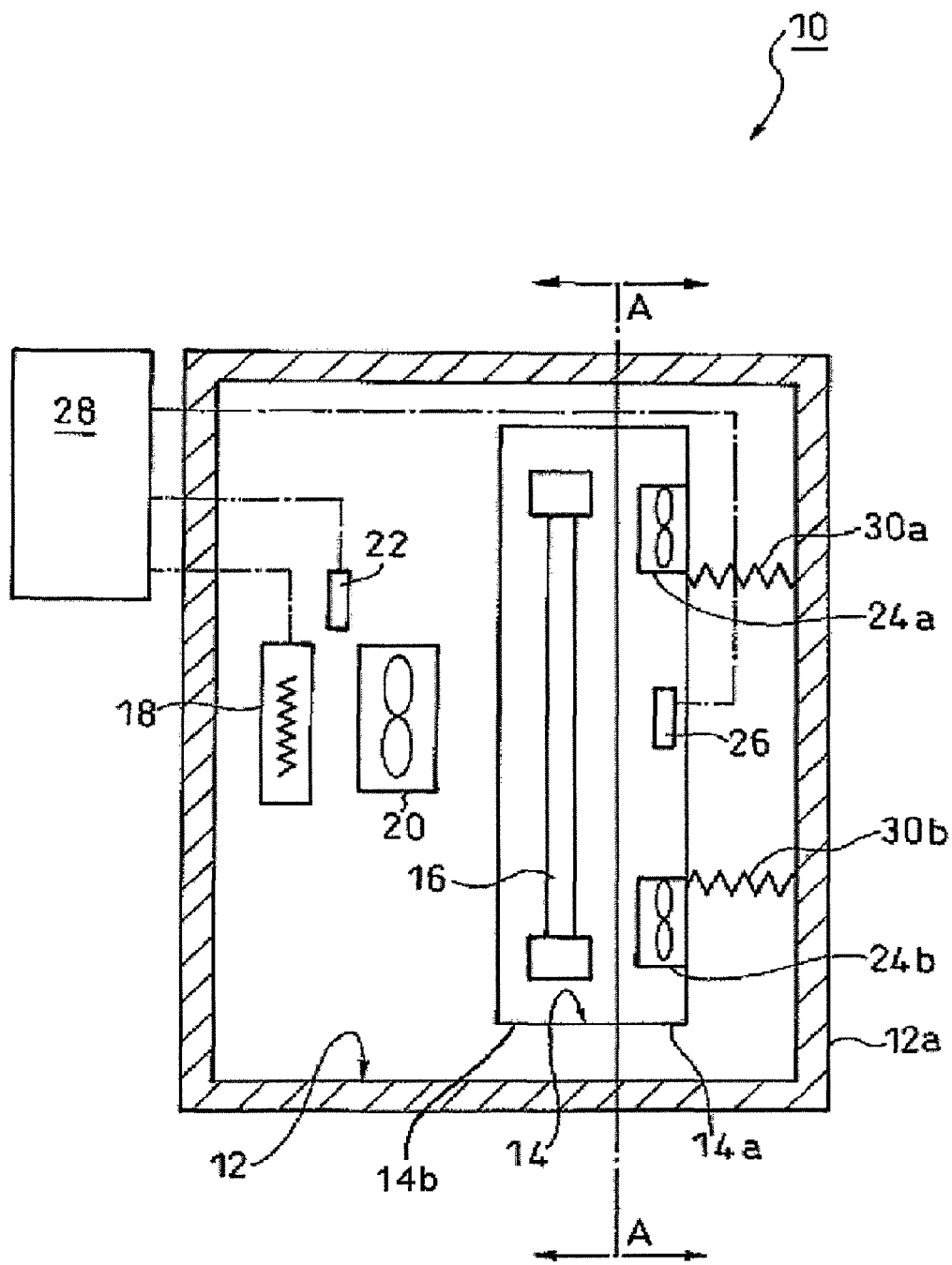
FIG. 1 is a diagram showing a column oven according to one embodiment of the present invention.

FIG. 1 shows an outline configuration of a column oven 10 according to an embodiment of the present invention.

The column oven 10 shown in FIG. 1 includes an outer chamber 12 and an inner chamber 14 disposed in the outer chamber 12. All walls of the outer chamber are a certain distance from all walls of the inner chamber so that air can circulate between them.

In the inner chamber 14, column 16 which is to be heated is disposed.

In the outer chamber 12, a heater 18 for increasing the temperature, a fan 20 for circulating the air heated by the heater 18, and a temperature sensor 22 for detecting the temperature inside the outer chamber, that is, the temperature outside the inner chamber, are disposed.

In the inner chamber 14, in addition to the column 16, fans 24a and 24b for circulating the air inside the inner chamber, and a temperature sensor 26 for detecting the temperature inside the inner chamber are also disposed.

The signals detected by the temperature sensor 22 for the outer chamber and the temperature sensor 26 for the inner chamber are sent to a temperature controller 28. The temperature controller 28 controls the amount of heat generated by of the heater 18.

A configuration of the column oven 10 according to the present invention is outlined as above. Details of the column oven 10 will be described below.

Column 16 is disposed in the inner chamber 14 of the column oven 10. In the column oven 10 according to the various embodiments of the present invention, a front portion 12a of the outer chamber wall (i.e. the right side in FIG. 1) is connected with a front portion 14a of the inner chamber wall by connecting members 30a and 30b made of elastic material so that the front portions don't contact each other directly. The front portion 12a of outer chamber wall and the front portion 14a of inner chamber wall can be moved to the right relative to line A-A in coordination with a front door of an enclosing apparatus which is not shown in FIG. 1.

By moving the two front portions to the right from line A-A on, it becomes easy to access the inside of the inner chamber 14 from the front side of the apparatus, and the column 16 can be easily put inside the inner chamber 14.

After column 16 is disposed and successive plumbing is completed, the front portion 12a of outer chamber wall and the front portion 14a of inner chamber wall are returned to the position shown in FIG. 1 in conjunction with closing the front door of the apparatus. Consequently, the inside of the outer chamber 12 is insulated from the outside, the front portion 14a of inner chamber wall is pressed tightly to a main body wall 14b of the inner chamber by the connecting members 30a and 30b made of elastic material, and the inner chamber is insulated from the outer chamber. In a state that the doors are closed, no portion of the outer chamber wall directly contacts the inner chamber wall.

Then, program for increasing temperature, which is correlated with the measurement desired, is initiated by operating the controller 28.

In order to raise the temperature of the column 16 to a desired temperature (e.g., 40° C.), the controller 28 supplies electricity to the heater 18 to generate heat. The air heated by the heater 18 circulates inside the outer chamber 12 using the fan 20 and heats inside of the inner chamber 14 through the inner chamber wall, which is spaced-apart from the outer chamber wall. The circulating heated air surrounding the whole wall surface of the inner chamber 14. The fans 24a and 24b disposed in the inner chamber 14 circulate the air inside the inner chamber 14 to equalize the temperature everywhere in the inner chamber 14 and heat the column 16.

As a result of testing by the inventors of the present invention, on/off operation of the heaters, ambient temperature changes around the column oven, and an uneven temperature inside the column oven can be considered as factors which affect for the column temperature which have the potential to adversely affect the result of measuring differential refractive index.

Among the factors, the effect of on/off operation of the heaters can be ruled out because small temperature changes inside the outer chamber are not transferred to the inner chamber due to being blocked by the inner chamber wall.

On the other hand, the outer chamber wall has a more or less uneven temperature because the outer surface of the outer chamber 12 is directly or indirectly affected by the temperature of the room where the column oven is placed. With conventional column ovens, this uneven temperature has caused an uneven temperature inside the column oven 10 which results in an uneven temperature of the column 16.

More specifically, in an analyzer which uses a differential refractometer requiring both a sample column and a reference column, even a difference in the locations between the sample column and the reference column will cause differences in the temperatures thereof, which overlaps with measurement results as noise. However, according to the column oven in the embodiments of the present invention, while uneven temperature is slightly caused in the outer chamber 12 in the same manner as with the conventional column ovens, any temperature difference attributed to the placement of columns seldom results because the air circulating inside the outer chamber 12 transfers heat uniformly by surrounding the whole wall surface of the inner chamber 14 and the fans insure an even, uniform temperature inside the inner chamber 12.

As a result, even when measuring differential refractive index, the column oven according to the present invention shows no temperature difference among a plurality of columns and can provide extremely highly-stable temperature control and a highly stable baseline.

In the present invention, aluminum or stainless steel may be used as the material for the wall of the inner chamber 14. To inhibit small temperature changes in the outer chamber 12 from transferring to the inner chamber 14, a material having low heat transfer capability and a good corrosion resistance, such as stainless steel, is preferably used.

Further, in the present invention, the column oven includes a temperature sensor for the inner chamber in addition to a temperature sensor for the outer chamber. However, it is possible to stabilize the temperature inside the inner chamber by using only a temperature sensor for the outer chamber though stabilization takes a little more time.

Further, in the present invention, though the column oven has no heater in the inner chamber, a preheater which is used only before temperature stabilization but which is not used during measurement of the differential refractive index may be disposed in the inner chamber. Thus a rapid rising of the temperature in the inner chamber is possible.

Figure 2:
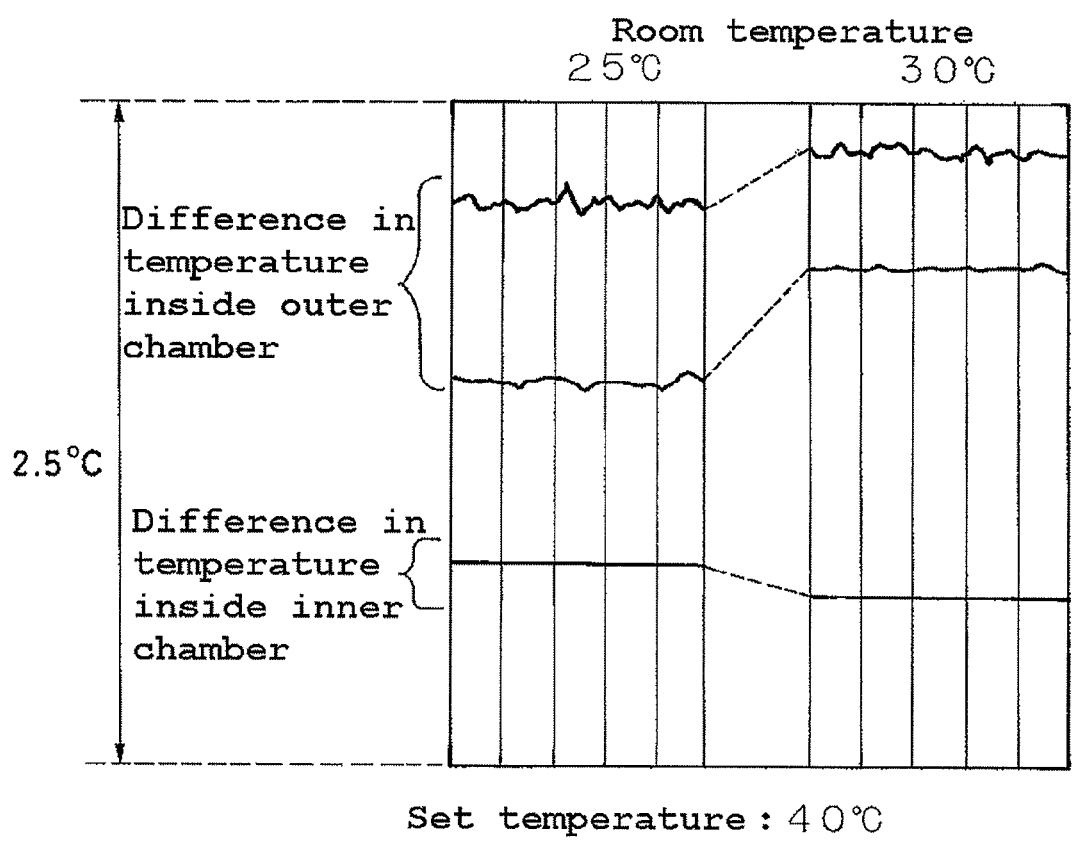
FIG. 2 is a graph showing a temperature-stabilizing effect of the column oven shown in FIG. 1.

FIG. 2 shows the measurement results of temperature distribution inside the outer chamber 12 and inside the inner chamber 14.

In FIG. 2, when a set temperature in the column oven 10 was 40° C., while the difference between a high temperature part and a low temperature part, that is, the difference in the uneven temperature inside the outer chamber 12 was about 0.6° C., the difference in the uneven temperature inside the inner chamber 14 was reduced to 0.05° C. While the temperature change, presumably attributed to on/off operations of the heater, at every point of the outer chamber was 0.05° C., such temperature change at every point of the inner chamber was only 0.01° C. or less. Comparing the temperature changes when the room temperature was 25° C. with the temperature changes when the room temperature was 30° C., the temperature changes inside the inner chamber were reduced to 0.05° C. while the temperature changes inside the outer chamber were 0.5° C.

As described above, the column oven according to the embodiments of the present invention can achieve highly excellent temperature stability and accuracy.

The inventors of the present invention next verified variations of baseline, detected by a differential refractometer, in the column oven according to the embodiment of the invention shown in FIG. 1 and in a column oven, as a comparative example, in which temperature was controlled by a heater disposed in an inner chamber of a double-chamber column oven.

As the column oven in which temperature was controlled by a heater disposed in an inner chamber of a double-chamber column oven, a conventional column oven having no inner chamber was used in a temperature-controlled room. Temperature control in the temperature-controlled room thus corresponded to temperature control in an outer chamber of the column oven of the present invention. As the column oven according to the present embodiment, the column oven shown in FIG. 1 was used.

Figure 3:
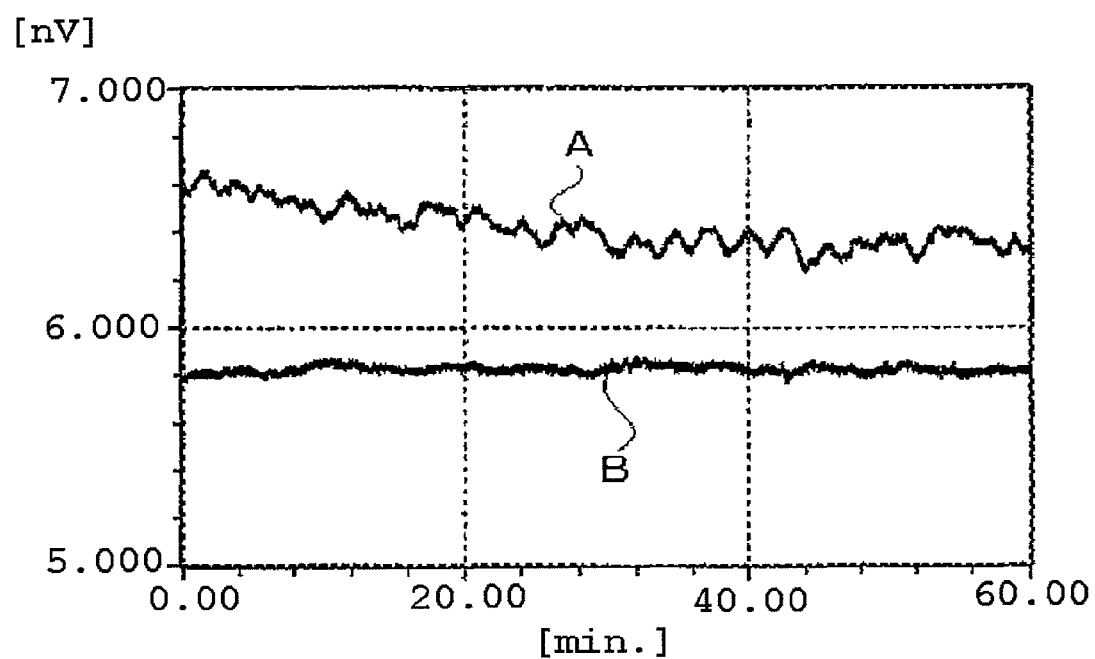
FIG. 3 is a graph showing variations in a baseline, detected by a differential refractometer, in a column oven according to the present invention and variations in a baseline, detected by a differential refractometer, in a column oven in which temperature is controlled by a heater disposed in an inner chamber of a double-chamber column oven.

FIG. 3 shows the results of variations of baseline, detected by a differential refractometer, in each column oven. In the column oven in which temperature was controlled by a heater disposed in the inner chamber, because small temperature changes attributed to on/off operation of the heater in the inner chamber would transfer to the columns directly, small variations in the baseline were detected by the differential refractometer, as shown by a line A in FIG. 3. In distinction, in the column oven according to the present embodiment, because small temperature changes attributed to on/off operation of the heater in the outer chamber did not transfer to the inner chamber, variations of the baseline detected by the differential refractometer could be kept smaller than those in the column oven having a heater in an inner chamber, as shown by a line B in FIG. 3.

The inventors of the present invention further verified variations of the baseline with respect to ambient temperature change, detected by a differential refractometer, in the apparatus having a double-chamber structure according to the present invention shown in FIG. 1 and in a conventional column oven having no inner chamber.

Figure 4:
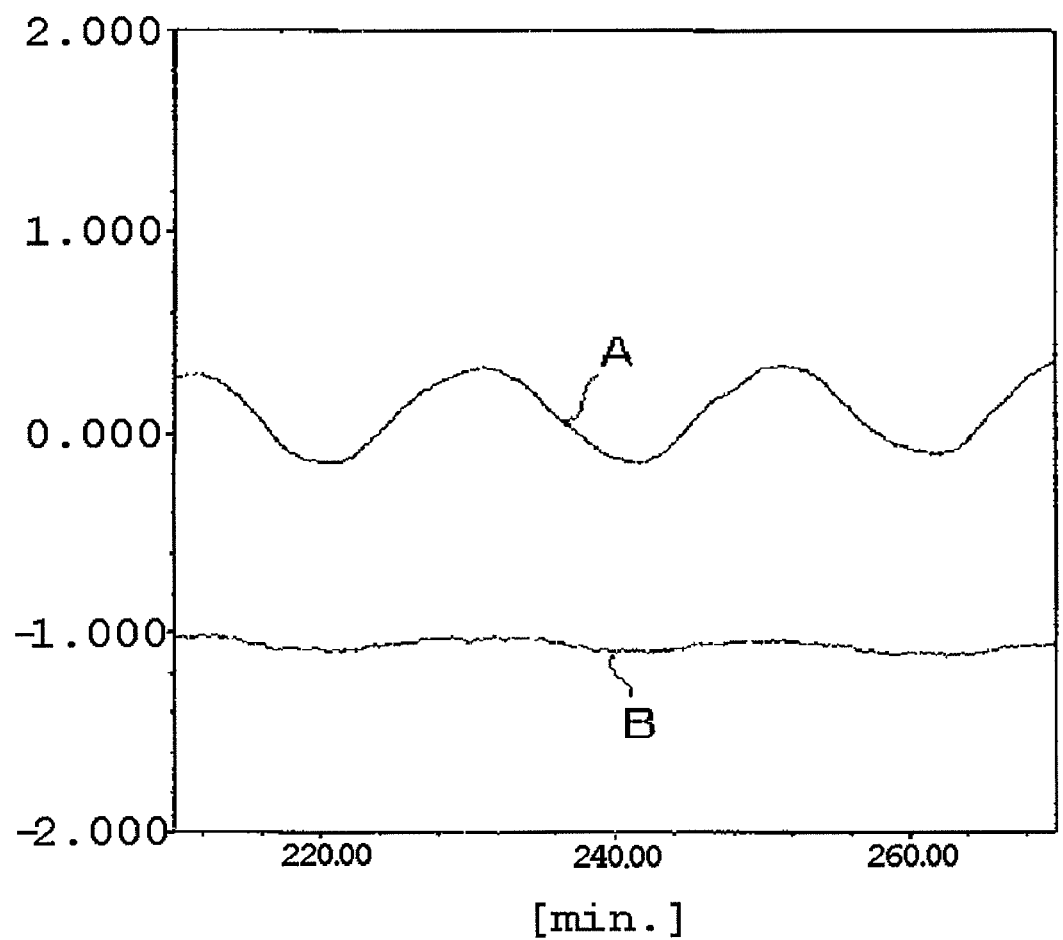
FIG. 4 is a graph showing variations in a baseline with respect to ambient temperature change, detected by a differential refractometer, in a column oven according to the present invention and variations in a baseline with respect to ambient temperature change, detected by a differential refractometer, in a conventional column oven having no inner chamber.

FIG. 4 shows the result of variations of the baseline, detected by a differential refractometer, in each column oven when the ambient temperature went up and down by 5° C. in 20 minute periods.

In the conventional column oven having no inner chamber, because the temperature inside the column oven varied corresponding to the ambient temperature change in the same manner as shown by the result of an outer chamber in FIG. 2, variations of baseline were detected by the differential refractometer, as shown by line A in FIG. 4.

In distinction, in the column oven of the present invention, because the temperature change in the inner chamber was smaller than the temperature change in the conventional column oven having no inner chamber as shown by in the result of an outer chamber in FIG. 2, variations of the baseline detected by the differential refractometer could be kept small, as indicated by line B in FIG. 4.

Figure 5:
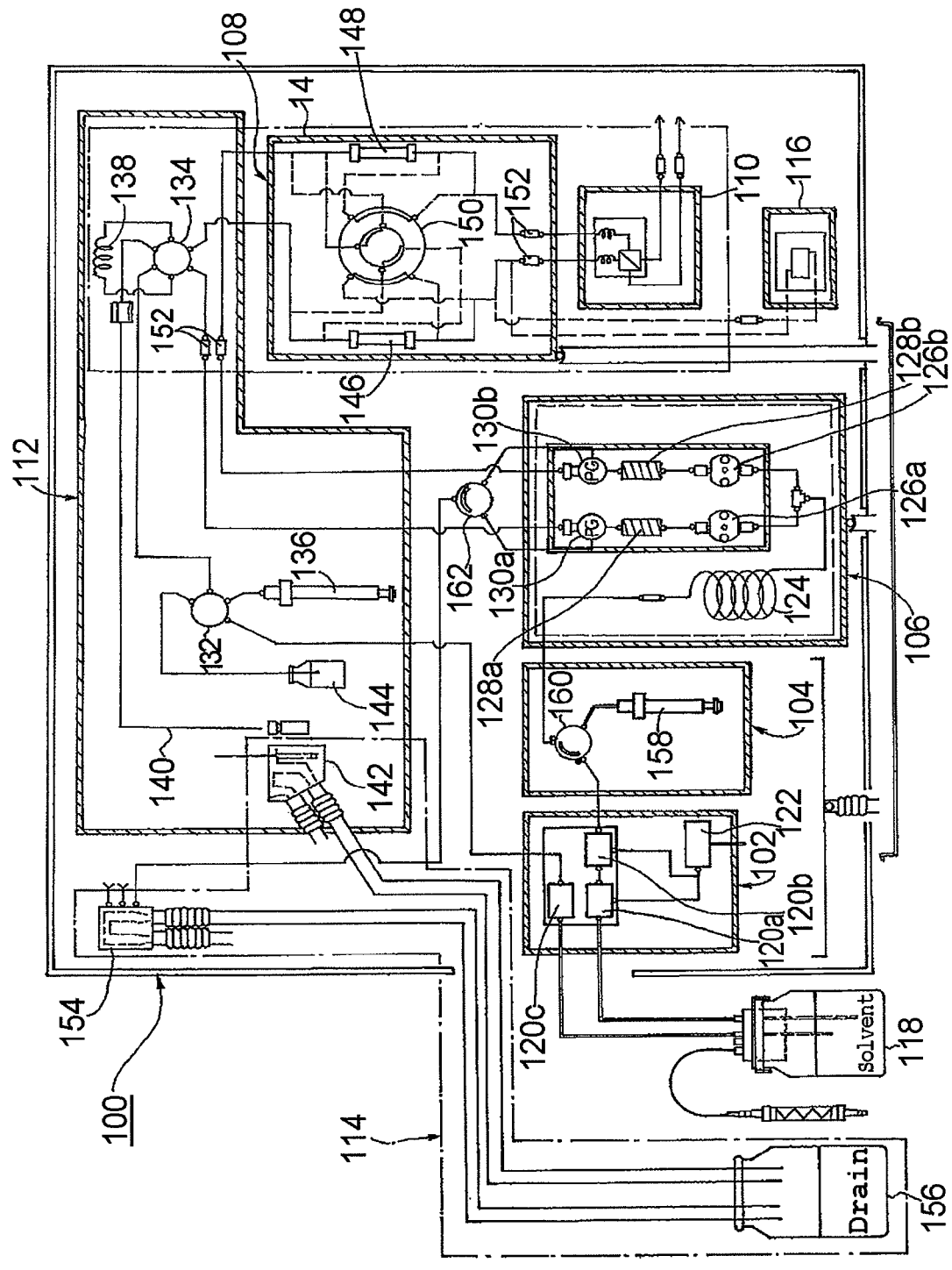
FIG. 5 is a diagram showing the configuration of a liquid chromatographic apparatus having a differential refractometer according to one embodiment of the present invention.

FIG. 5 shows a configuration of a liquid chromatographic apparatus using a column oven according to the embodiments of the present invention.

A liquid chromatographic apparatus 100 as shown in FIG. 5 includes a degassing unit 102, a purge unit 104, a pump oven unit 106, a column oven unit 108, a differential refractive index measuring unit 110, an injection unit 112, and a drain unit 114. As necessary, the liquid chromatographic apparatus 100 further can include a UV detecting unit 116 and other conventional devices as optional units.

A solvent from solvent bath 118 is degassed by the degassing unit 102 and flows into the pump oven unit 106 through the purge unit 104. The solvent preheated by the pump oven unit 106 is divided into two routes: one is a sample flow route and the other is a reference flow route. The solvent which flows into the sample flow route passes through a sample column 146 in the column oven unit 108, and the solvent which flows into the reference route passes through a reference column 148 in the column oven unit 108.

The refractive index of each solvent is then measured by the differential refractive index measuring unit 110. In the sample flow route, a sample is injected by the injection unit 112. It is also possible to configure the apparatus so that the measured sample solution and the measured reference solution are discarded or collected through the drain unit 114.

The degassing unit 102 includes degassing chambers 120a, 120b, and 120c. The solvent passing through porous tubes (not shown) inside the degassing chambers is exposed to a vacuum and degassed by a vacuum pump 122 which is controlled to be at a constant pressure. Though there are some degassing chambers 120 made of resin, generally, a degassing chamber made of aluminum is used when an organic solvent is used. However, when a halogenated solvent such as chloroform is used, a degassing chamber made of stainless steel is preferably used because a degassing chamber made of aluminum is sometimes corroded.

The pump oven unit 106 includes a preheating coil 124 for the solvent, a sample-solution forwarding pump 126a, a reference-solution forwarding pump 126b, bourdon tube accumulators 128a and 128b, a pressure gauge (labeled PG) and filter 130a, and a pressure gauge (labeled PG) and filter 130b. The inside of the pump oven unit 106 is kept at constant temperature. The degassed solvent is heated to a certain temperature by the preheating coil 124 for the solvent, and then the solvent is divided into a sample flow route and a reference flow route. Each solvent flow is transferred through the corresponding solution forwarding pump 126, bourdon tube accumulator 128, and pressure gauge 130.

The injection unit 112 injects a predetermined amount of sample into the solvent flowing from the sample flow route. Thus, the injection unit 112 includes a sampling valve 132, an injection valve 134, and a syringe 136. The injection valve 134 is configured so as to be capable of linking the sample flow route directly by connecting one of the ports to another adjacent port. Initially, the sample-solution forwarding pump 126a, the injection valve 134, the sample flow loop 138, the injection valve 134, and the sample column 146 are connected in that order. By switching with the valve 134, the sample loop 138, the injection valve 134, the sampling valve 132, and a depressurizing bottle 144 are connected in that order, and the pressure inside the sample flow loop 138 is reduced. By then switching with the injection valve 134, the syringe 136, the sampling valve 132, the injection valve 134, the sample flow loop 138, and the injection valve 134 are connected in that order, and a sample is injected into the sample loop 138 by suction applied by the syringe 136. By then switching with the injection valve 134, the sample-solution forwarding pump 126a, the injection valve 134, the sample loop 138, the injection valve 134, and the sample column 146 are connected in that order, and the sample in the sample loop 138 is injected into the sample flow route.

When a solvent is filled in the syringe 136, by switching with the sampling valve 132, the solvent in the solvent bath 118 is aspirated up by the syringe 136 through the degassing unit 102. When a sample-aspirating needle 140 is washed, a wash solvent is filled in a needle-wash port 142, and a tip of the needle 140 is soaked in the wash solvent to wash the same.

The column oven unit 108 includes the sample column 146, the reference column 148, and a column switching valve 150. In this column oven unit 108, the sample and solvent flowing from the sample flow route are transferred to the sample column 146, and the sample and solvent flowing from the reference flow route are transferred to the reference column 148. By switching with the column switching valve 150, the routes can be switched between the sample column 146 and the reference column 148.

In FIG. 5, the column oven shown in FIG. 1, which has an outer chamber 12 and an inner chamber 14, is used. The outer chamber 12 also includes the injection valve 134, which enables one to inject a sample which is kept at a constant temperature.

Each solution passed through the sample column 146 or the reference column 148 is transferred to the differential refractive index measuring unit 110, the refractive index measured as desired, and then transferred to the drain unit 114.

The drain unit 114 includes a drain port 154 and a drain bottle 156. The drain port 154 discharges solution flowing from the differential refractive index measuring unit 110. During discharge, any change of fluid pressure in tubes for discharging fluid is prevented from occurring by fixing a discharge outlet in a certain position while a change of back pressure is prevented from occurring by adopting a discharge structure that the solution slides down the inner wall surface of the drain bottle 156 so as to prevent falling in droplets.

In the embodiments of the present invention, the purge unit 104 includes a syringe 158 and a stop valve 160. In a conventional chromatographic apparatus, when solvent is replaced after discharging the solution in each tube for fluid, such as when tubes for fluid are washed, it sometimes takes an extremely long time to aspire up the solvent from a solvent bath 118 using only a pump 126. In the embodiments of the present invention, the syringe 158, the stop valve 160, the degassing unit 102, and the solvent bath 118 are connected in that order by switching with the stop valve 160, and the solvent is aspirated up by the syringe 158. The syringe 158, the preheating coil 124, and the pump 126 are connected in that order by switching with the stop valve 160 again, and the solvent is filled in the pump 126 by injecting with the syringe 158. During purging the solvent, a countercurrent flow of solvent during filling the solvent in the pump 126 can be prevented from occurring because the pump 126 and like units are not connected to the solvent bath 118. During purging the solvent, it is preferred that a tube for discharging fluid of the pump 126 be connected to the drain port 154 by switching with the drain valve 162.

In the embodiments of the present invention, when there is a time interval between measurements, washing a needle with solvent prior to measurement is preferably conducted to eliminate any effects from volatilization of the solvent inside the needle 140.

Figure 6:
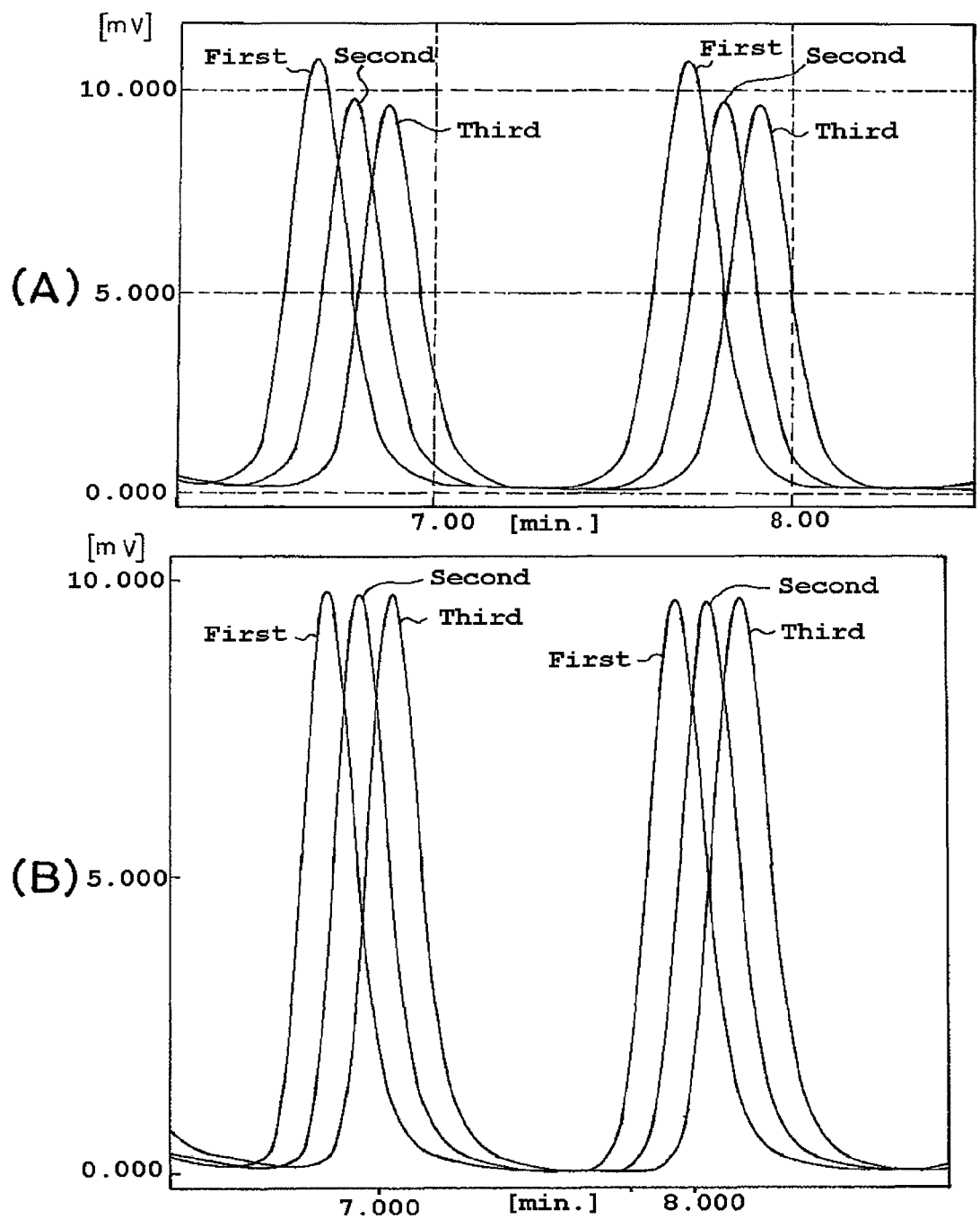
FIG. 6 is a graph showing measurement results when there is a receding liquid level in a passage of a needle tip and measurement results when there is no receding liquid level in a passage of a needle tip.

In the conventional chromatographic apparatus, when aspirating up and measuring a certain amount of one sample is repeated several times, only the detected value for the first time is higher than the others, as shown in FIG. 6(A).

In this respect, in the apparatus according to the present invention, excellent reproducibilty, as shown in FIG. 6(B) can be achieved by, prior to the first measurement, contacting a needle tip to a solvent to replenish a receding amount of the solvent in a passage of needle tip.

What is claimed is:

1. A column oven comprising
an outer chamber and an inner chamber disposed in the outer chamber;
one or more columns disposed in the inner chamber;
wherein the outer chamber includes one or more heaters, one or more fans for the outer chamber for circulating air heated by the heaters, and a temperature sensor for the outer chamber for detecting the temperature inside the outer chamber;
wherein the inner chamber having no heater in the inner chamber includes one or more fans for the inner chamber; and
a controller for controlling power supplied to the heaters according to the temperature detected by the temperature sensor for the outer chamber.

2. A column oven comprising:
an outer chamber and an inner chamber disposed in the outer chamber;
one or more columns disposed in the inner chamber;
wherein the outer chamber includes one or more heaters, one or more fans for the outer chamber for circulating air heated by the heaters, and a temperature sensor for the outer chamber for detecting the temperature inside the outer chamber;
wherein the inner chamber having no heater in the inner chamber includes one or more fans for the inner chamber and a temperature sensor for the inner chamber for detecting the temperature inside the inner chamber; and
a temperature controller for controlling the power supplied to the heaters by comparing the temperature detected by the temperature sensor for the outer chamber with a target temperature in the outer chamber which is set based on the temperature detected by the temperature sensor for the inner chamber.

3. The column oven according to claim 1 comprising:
one or more sample columns and one or more reference columns, disposed in the inner chamber; and
wherein the column oven is mounted in a liquid chromatographic apparatus having a differential refractometer.

4. The column oven according to claim 1 comprising:
wherein each of the outer chamber and the inner chamber has a door, and the door of the outer chamber is connected to the door of the inner chamber by one or more connecting members made of elastic material; and
wherein the door of the inner chamber opens in conjunction with opening the door of the outer chamber and the door of the inner chamber closes in conjunction with closing the door of the outer chamber in a state that the door of the inner chamber is spaced-apart from the door of the outer chamber.

5. The column oven according to claim 2 comprising:
one or more sample columns and one or more reference columns, disposed in the inner chamber; and
wherein the column oven is mounted in a liquid chromatographic apparatus having a differential refractometer.

6. The column oven according to claim 2 comprising:
wherein each of the outer chamber and the inner chamber has a door, and the door of the outer chamber is connected to the door of the inner chamber by one or more connecting members made of elastic material; and
wherein the door of the inner chamber opens in conjunction with opening the door of the outer chamber and the door of the inner chamber closes in conjunction with closing the door of the outer chamber in a state that the door of the inner chamber is spaced-apart from the door of the outer chamber.

7. The column oven according to claim 3 comprising:
wherein each of the outer chamber and the inner chamber has a door, and the door of the outer chamber is connected to the door of the inner chamber by one or more connecting members made of elastic material; and
wherein the door of the inner chamber opens in conjunction with opening the door of the outer chamber and the door of the inner chamber closes in conjunction with closing the door of the outer chamber in a state that the door of the inner chamber is spaced-apart from the door of the outer chamber.

* * * * *